(12) United States Patent
Vogt

(10) Patent No.: US 9,320,897 B2
(45) Date of Patent: Apr. 26, 2016

(54) INDUCTIVE LINK COUPLED MINIATURE INTRA-COCHLEAR ELEMENTS

(71) Applicant: MED-EL Elektromedizinische Geraete GmbH, Innsbruck (AT)

(72) Inventor: Gerhard Vogt, München (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 226 days.

(21) Appl. No.: 13/767,033

(22) Filed: Feb. 14, 2013

(65) Prior Publication Data

US 2014/0228901 A1    Aug. 14, 2014

(51) Int. Cl.
| | |
|---|---|
| *A61N 1/36* | (2006.01) |
| *A61N 5/06* | (2006.01) |
| *A61N 1/05* | (2006.01) |
| *H04R 25/00* | (2006.01) |
| *A61F 11/04* | (2006.01) |

(52) U.S. Cl.
CPC .......... *A61N 1/36032* (2013.01); *A61N 1/0541* (2013.01); *A61N 5/0622* (2013.01); *A61F 11/04* (2013.01); *A61N 2005/0605* (2013.01); *H04R 25/606* (2013.01)

(58) Field of Classification Search
CPC .. A61N 1/36032; A61N 1/0541; A61F 11/04; H04R 25/606

USPC ............................................ 607/1, 2, 32, 137
See application file for complete search history.

(56) References Cited

U.S. PATENT DOCUMENTS

| | | | | |
|---|---|---|---|---|
| 5,405,367 | A  * | 4/1995 | Schulman et al. | 607/61 |
| 8,060,218 | B2 * | 11/2011 | Singh et al. | 607/116 |
| 2004/0260367 | A1* | 12/2004 | De Taboada et al. | 607/88 |
| 2010/0174329 | A1* | 7/2010 | Dadd et al. | 607/3 |
| 2011/0137393 | A1* | 6/2011 | Pawsey et al. | 607/137 |

* cited by examiner

*Primary Examiner* — Niketa Patel
*Assistant Examiner* — Lindsay G Hankins
(74) *Attorney, Agent, or Firm* — Sunstein Kann Murphy & Timbers LLP

(57) ABSTRACT

An implantable stimulation device is described which includes a flexible carrier member for implantation adjacent to target neural tissue. Carrier wires are embedded within the carrier member for conducting electrical signals. At least one active interface device also is within the carrier member and includes a hermetically sealed device housing without penetration by any electrical conductor, an active interface element within the device housing, an inductive link arrangement providing an electrical connection between the active interface element and a terminal end of one of the carrier wires, and an outer interface surface adjacent to the target neural tissue that provides a communication link between the adjacent target neural tissue and the active interface element.

9 Claims, 2 Drawing Sheets

INDUCTIVE LINK COUPLED MINIATURE INTRA-COCHLEAR ELEMENTS

TECHNICAL FIELD

The present invention relates to active signal devices used in neural implant systems such as cochlear implants.

BACKGROUND ART

Neural implant systems such as cochlear implants deliver stimulation signals to target neural tissue. For example, FIG. 1 shows a cochlear implant arrangement where an implant electrode 100 penetrates through a cochleostomy opening 102 into a patient cochlea 101. The intra-cochlear portion of the implant lead is referred to as the electrode array 103 and includes multiple stimulation contacts 104 that deliver electrical stimulation signals to auditory neural tissue within the cochlea 101.

Existing commercial neural implant systems are based on the use of electrical stimulation signals, but there have been some recent proposals to stimulate nerves either optically or optically in combination with electrical stimulation. A light source can be generated locally in the vicinity of the nerve (e.g. by LEDs or micro-lasers), or it can be generated remotely and transported to the nerve (e.g., by optical fiber).

U.S. Patent Publication 20100174329 described a proposed arrangement for combined optical and electrical neural stimulation. The general ideas of such an arrangement were broadly discussed, but specific structural details of the optical stimulation arrangement were scant. For example, only fleeting mention was made of optical adjustment structures. Each optical stimulation contact was described as a single individual light source. WO 2007013891 also described an optical stimulation arrangement for cochlear implants but again seemed to offer little specific discussion of controlling the optics beyond suggesting that it might be useful to arrange some combination of a mirror, lens or prism. Optical stimulation of nerves was also discussed in US 20060129210 and US 20100114190, but again, some structural details are sketchy or unaddressed. US2012 0197374 described an implant carrier member with optical stimulation contacts having multiple optical sub-elements to control the shape and direction of the optical stimulation field.

SUMMARY

Embodiments of the present invention are directed to an implantable stimulation device which includes a flexible carrier member for implantation adjacent to target neural tissue. Carrier wires are embedded within the carrier member for conducting electrical signals. At least one active interface device also is within the carrier member and includes a hermetically sealed device housing without penetration by any electrical conductor, an active interface element within the device housing, an inductive link arrangement providing an electrical connection between the active interface element and a terminal end of one of the carrier wires, and an outer interface surface adjacent to the target neural tissue that provides a communication link between the adjacent target neural tissue and the active interface element.

The active interface device may be an optical stimulation device for delivering an optical stimulation signal to the adjacent target neural tissue, for example, a vertical cavity surface emitting laser (VCSEL) or a light emitting diode (LED). Or the active interface device may be an optical sensor device for sensing an optical condition of the adjacent target neural tissue.

The inductive link arrangement may include an outer inductive coil outside the device housing connected to the terminal end of the carrier wire, and an inner inductive coil within the device housing connected to the active interface element and inductively linked to the outer inductive coil to provide the electrical connection between the active interface element and the terminal end of the carrier wire. In addition, the active interface device may include program control logic within the device housing for programmable control of the active interface element.

The device housing may be made of glass material. The carrier member also may include conventional stimulation contacts located at terminal ends of the carrier wires for delivering electrical stimulation signals to adjacent target neural tissue. The carrier member may have multiple active interface devices.

The target neural tissue may be auditory neural tissue and the stimulation device may be a cochlear implant device. Or the target neural tissue may be vestibular neural tissue and the stimulation device may be a vestibular implant device.

DETAILED DESCRIPTION

One challenge with implanting active devices such as optical devices into patient tissue such as into the cochlea is to provide for proper packaging of the device. For safety reasons the device packaging needs to hermetically enclose the active element, be suitable for miniaturization, fulfill biocompatibility requirements and ensure device reliability. Electrically, it is important to avoid developing unintended dc currents between the device and the adjacent tissue and also to avoid short circuits especially for multiple power lines on device surfaces. And for optical devices which detect or emit electromagnetic radiation, the device package needs to be of a material of suitable transparency. Most conventional implant packaging materials are not optically transparent. Some polymer materials might be transparent, but these are problematic with regards to the hermeticity requirements.

Figure 1:
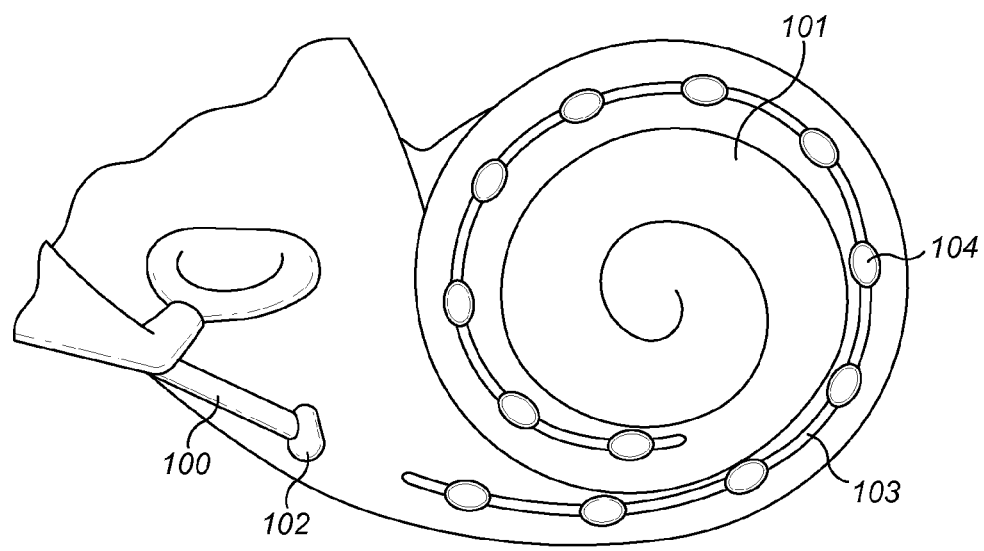
FIG. 1 shows a cochlear implant stimulation arrangement.
Figure 2:
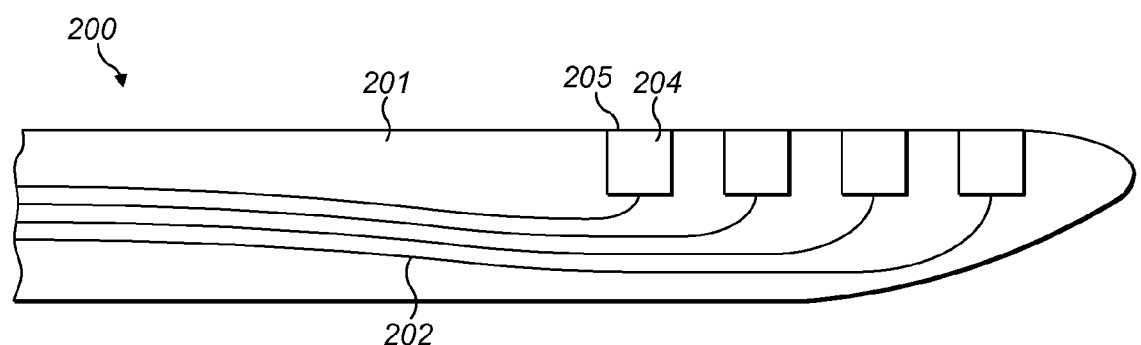
FIG. 2 shows a side view of an implantable stimulation device according to one or more embodiments of the present invention.

FIG. 2 shows a side view of an implantable stimulation device according to one or more embodiments of the present invention which is directed to an implantable stimulation device 200 which includes a flexible carrier member 201 for implantation adjacent to target neural tissue. The target neural tissue may be auditory neural tissue and the stimulation device may be a cochlear implant device. Or the target neural tissue may be vestibular neural tissue and the stimulation device may be a vestibular implant device. Typically for applications such as a cochlear implant, the carrier member 201 is made of very flexible polymer material to minimize trauma to the tissue into which it is inserted. Multiple carrier wires 202 are embedded within the carrier member 201 for conducting electrical signals between the distal wire ends and a proximal implanted processor (not shown).

One or more active interface devices 203 also are held within the carrier member 201 with an outer interface surface 205 that is positioned adjacent to the target neural tissue and which provides a communication link with the adjacent target neural tissue. In the embodiment shown in FIG. 2, the carrier member 201 contains multiple active interface devices 203. In some embodiments, the carrier member 201 also may include conventional electrical stimulation contacts located at terminal ends of some of the carrier wires 202 for delivering conventional electrical stimulation signals to adjacent target neural tissue. For example, in some embodiments, the basal end of the carrier member 201 may have conventional electrical stimulation contacts and the apical end of the carrier member 201 may have one or more active interface devices 203.

Figure 3:
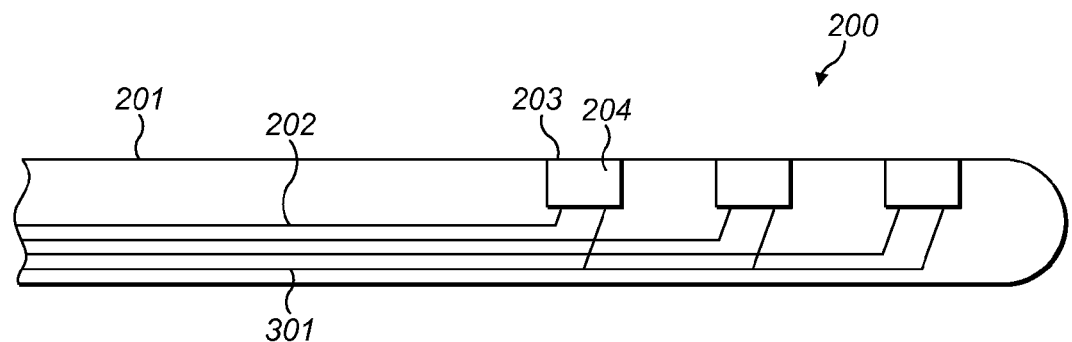
FIG. 3 shows a side view of an implantable stimulation device according to another embodiment of the present invention.

FIG. 3 shows a side view of an implantable stimulation device 200 having a single common ground wire 300 that provides a common ground/circuit return path for multiple carrier wires 202 and multiple interface devices 203. In other embodiments, there may be two wires per interface device, significantly more wires overall in the entire implantable stimulation device 200 than for using a single common ground wire 300. Minimizing the total number of wires by using a single common ground wire 300 maximizes the flexibility of the carrier member 201. More generally, the interfaces devices may be grouped together in groups of two or three which share a common ground wire. thus an embodiment with nine interface devices 203 might have three common ground wires 301, each providing a circuit return path for a grouping of three interface devices 203, with the interface devices 203 in each such grouping being sequentially stimulated. This compromise avoids a current limit on the ground wire 301 while still minimizing the number of overall wires and thereby maintaining flexibility of the carrier member 201.

Figure 4:
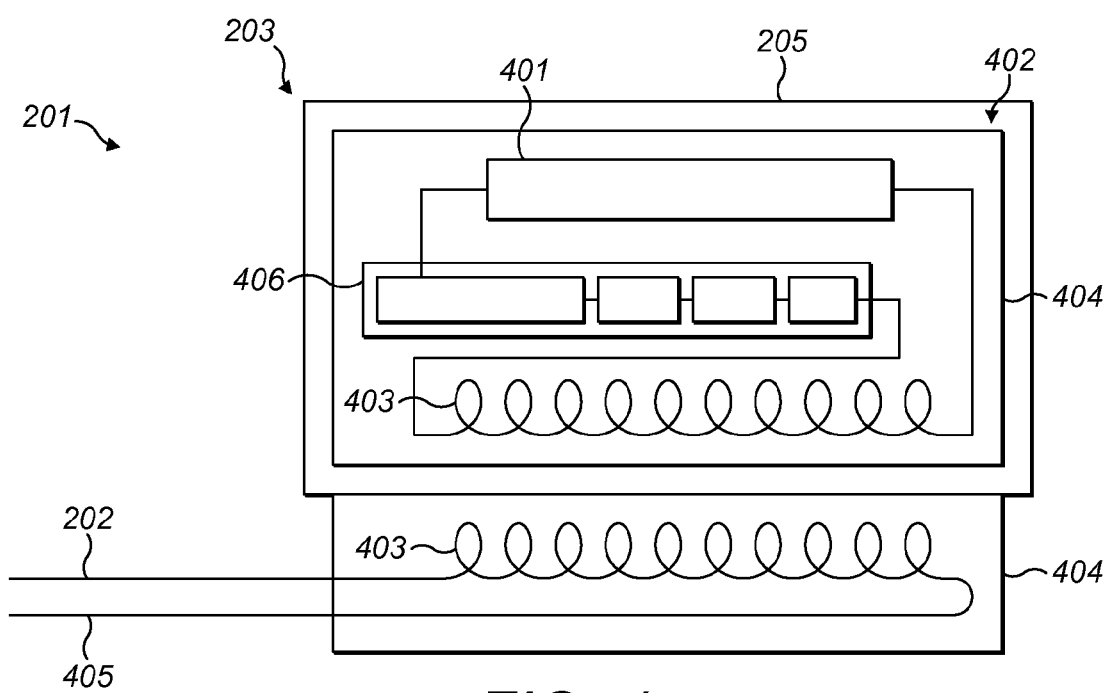
FIG. 4 shows greater structural detail of the active interface device according to an embodiment of the present invention.

FIG. 4 shows greater structural detail of the active interface device 203 according to a specific embodiment of the present invention. The active interface device 203 includes a hermetically sealed device housing 402 without any penetration by any electrical conductor, and an active interface element 401 is within the device housing 402. The active interface device 203 specifically may be a hermetically enclosed optical stimulation device for delivering an optical stimulation signal to the adjacent target neural tissue so that, for example, the active interface element 401 may specifically be a vertical cavity surface emitting laser (VCSEL) or a light emitting diode (LED).

In some embodiments, the active interface device 203 may include a sensor device for sensing one or more conditions of the adjacent target neural tissue such as light intensity, temperature and/or humidity, in which case the active interface element 401 includes a sensor element. For example, the active interface device 203 may be a photo-detector sensor that measures the optical transparency of cochlear fluid adjacent to the outer interface surface 205 to detect the murkiness of the cochlear fluid to adaptively adjust the intensity of optical stimulation (and/or account for aging effects on the structural elements such as LEDs).

An inductive link arrangement 403 provides an electrical connection between the active interface element 401 and a terminal end of one of the carrier wires 202 (and a common return line 405) without penetrating the device housing 402 in order to communicate electrical signals, for example power and/or information signals for or from the active interface element 401. In the embodiment shown in FIG. 4, the inductive link arrangement 403 includes an outer inductive coil outside the device housing 402 connected to the terminal end of the carrier wire 202 (and the common return line 405) and an inner inductive coil within the device housing 402 connected to the active interface element 401. Rather than just planar inductive coils, in some embodiments, the inductive link arrangement 403 may have an outer coil that entirely surrounds the active interface device 203 in a solenoid type winding that leaves open top and bottom regions.

In any case, the position of the coils in the inductive link arrangement 403 should be fixed so as to not require any kind of alignment optimization adjustments, for example, by molding polymer material 404 around the outer coil of the inductive link arrangement 403 to hold it in place against the device housing 402. In the embodiment shown in FIG. 4, the structures within the device housing 402 also are embedded in polymer material 404.

In addition, the active interface device 203 shown in FIG. 3 also includes optional program control logic 406 within the device housing 402 for programmable control of the active interface element 401 as well as a current regulator/limiter, and/or a circuit capacitance also contained in the block labeled 406. Such program control logic 406 may provide, for example, one or more programming modes for operation of the active interface device 203, especially where there may be multiple light sources and/or active interface devices 203 to be controlled. The program control logic 406 may be an integral part of the active interface device 203, for example, the active interface device 203 and the program control logic 306 may be on a common silicon substrate.

It is important that the material used for the device housing 402 (or at least its outer surface 205) be both optically transparent and allow the penetration of magnetic fields, for example, using glass compounds. But one general problem with molding of materials such as glass around electronic circuits is the heat needed to melt the mold material, which can damage or destroy the electrical elements. Thus a standard packaging assembly procedure may be more favorable which assembles the active interface element 401, the inner inductive coil and any other device circuit elements within an assembly of planar housing surfaces which can be sealed by various specific means such as glass frit bonding, laser welding and/or electric bonding.

Although various exemplary embodiments of the invention have been disclosed, it should be apparent to those skilled in the art that various changes and modifications can be made which will achieve some of the advantages of the invention without departing from the true scope of the invention.

What is claimed is:
1. An a stimulation device comprising:
 a flexible carrier member having a proximal end coupled to an implanted cochlear implant signal processor and a distal electrode array portion with a plurality of stimulation contacts configured for implantation through a cochlear opening into a patient cochlea adjacent to target neural tissue;
 a plurality of carrier wires embedded within the carrier member configured for conducting electrical signals from the implanted cochlear implant processor through the carrier member into the patient cochlea, each carrier wires having a distal end connected to a stimulation contact for delivering the electrical signals to the adjacent target neural tissue; and
 at least one of the stimulation contacts comprising an active interface device embedded within the carrier member and including:

i. a hermetically sealed device housing without penetration by any electrical conductor;
ii. an active interface element within the device housing configured for processing the electrical signals,
iii. an inductive link arrangement configured to provide an electrical connection between the active interface element and a terminal end of one of the carrier wires to couple the electrical signals from the terminal end of the carrier wire into the hermetically sealed device housing to the active interface element, and
iv. an outer interface surface adjacent to the target neural tissue configured to provide a communication link between the adjacent target neural tissue and the active interface element.

2. A stimulation device according to claim 1, wherein the active interface device is an optical stimulation device configured to deliver an optical stimulation signal to the adjacent target neural tissue.

3. A stimulation device according to claim 2, wherein the active interface element includes a vertical cavity surface emitting laser (VCSEL).

4. A stimulation device according to claim 2, wherein the active interface element includes a light emitting diode (LED).

5. A stimulation device according to claim 1, wherein the active interface device includes a sensor device configured to sense a condition of the adjacent target neural tissue.

6. A stimulation device according to claim 5, wherein the sensor device is an optical sensor configured to sense an optical condition of the adjacent target neural tissue.

7. A stimulation device according to claim 1, wherein the inductive link arrangement includes:
i. an outer inductive coil outside the device housing connected to the terminal end of the carrier wire, and
ii. an inner inductive coil within the device housing connected to the active interface element and inductively linked to the outer inductive coil to provide the electrical connection between the active interface element and the terminal end of the carrier wire.

8. A stimulation device according to claim 1, wherein the active interface device further comprises:
program control logic within the device housing configured to provide programmable control of the active interface element.

9. A stimulation device according to claim 1, wherein the device housing is made of glass material.

* * * * *